US00RE49848E

(19) United States
(12) Reissued Patent
Calasso et al.

(10) Patent Number: US RE49,848 E
(45) Date of Reissued Patent: Feb. 27, 2024

(54) SYSTEM AND METHODS FOR MEDICAMENT INFUSION

(71) Applicant: Medirio SA, Visp (CH)

(72) Inventors: Irio Giuseppe Calasso, Arth (CH); Luca Calasso, Zurich (CH)

(73) Assignee: Medirio S.A., Visp (CH)

(21) Appl. No.: 17/161,330

(22) Filed: Jan. 28, 2021

Related U.S. Patent Documents

Reissue of:
(64) Patent No.: 10,188,788
Issued: Jan. 29, 2019
Appl. No.: 13/139,843
PCT Filed: Dec. 24, 2009
PCT No.: PCT/CH2009/000411
§ 371 (c)(1),
(2) Date: May 24, 2012
PCT Pub. No.: WO2010/072010
PCT Pub. Date: Jul. 1, 2010

(30) Foreign Application Priority Data

Dec. 24, 2008 (WO) ..... PCTCH2008000550

(51) Int. Cl.
*A61M 5/14* (2006.01)
*A61M 5/142* (2006.01)
(Continued)

(52) U.S. Cl.
CPC ..... *A61M 5/1413* (2013.01); *A61M 5/14* (2013.01); *A61M 5/14244* (2013.01); *A61M 5/14248* (2013.01); *A61M 5/168* (2013.01); *A61M 5/20* (2013.01); *A61M 5/50* (2013.01); *A61M 2005/14268* (2013.01); *A61M 2005/2073* (2013.01); *A61M 2205/8237* (2013.01); *A61M 2205/8287* (2013.01)

(58) Field of Classification Search
None
See application file for complete search history.

(56) References Cited

U.S. PATENT DOCUMENTS 4,559,037 A * 12/1985 Franetzki ..... A61M 5/172 604/151
5,314,453 A * 5/1994 Jeutter ..... A61N 1/3787 607/60
(Continued)

FOREIGN PATENT DOCUMENTS

WO 02068015 A2 9/2002
WO WO 2002068015 9/2002
(Continued)

*Primary Examiner* — Glenn K Dawson
(74) *Attorney, Agent, or Firm* — Fish & Richardson P.C.

(57) ABSTRACT

System for trans-dermal delivery of doses of a medicament, comprising a delivery device to be placed in dermal contact with a patient, the delivery device comprising a reservoir for holding a medicament to be delivered, a trans-dermal injection element for delivering doses of the medicament to the patient, a control unit for controlling the delivery of the medicament when activated, the system further comprising a separate hand-held drive device to be temporarily placed in proximity of the delivery device when a dose of medicament is required, the drive device comprising an activation unit for activating the control unit of the delivery device.

34 Claims, 8 Drawing Sheets

(51) Int. Cl.

| | |
|---|---|
| ***A61M 5/20*** | (2006.01) |
| ***A61M 5/50*** | (2006.01) |
| ***A61M 5/168*** | (2006.01) |
| ***A61M 5/145*** | (2006.01) |

(56) References Cited

U.S. PATENT DOCUMENTS

| | | | | |
|---|---|---|---|---|
| 5,350,413 | A | 9/1994 | Miller | |
| 5,643,194 | A * | 7/1997 | Negre | A61M 27/006 137/385 |
| 5,827,219 | A * | 10/1998 | Uber | A61M 5/16827 604/30 |
| 6,740,059 | B2 | 5/2004 | Flaherty | |
| 9,675,752 | B2 * | 6/2017 | Christensen | A61M 5/148 |
| 2002/0169439 | A1 * | 11/2002 | Flaherty | A61P 9/10 604/891.1 |
| 2005/0171512 | A1 * | 8/2005 | Flaherty | G16H 20/17 604/890.1 |
| 2007/0106269 | A1 * | 5/2007 | Hood | A61K 9/0009 280/736 |
| 2008/0129486 | A1 * | 6/2008 | Jeckelmann | A61M 5/14248 340/539.12 |
| 2008/0319381 | A1 * | 12/2008 | Yodfat | A61M 5/1723 604/65 |
| 2010/0137790 | A1 * | 6/2010 | Yodfat | A61M 5/14248 604/67 |
| 2010/0217353 | A1 * | 8/2010 | Forsell | H02J 50/80 607/61 |
| 2010/0292759 | A1 * | 11/2010 | Hahn | A61N 1/36038 607/57 |
| 2010/0305663 | A1 * | 12/2010 | Aghassian | A61N 1/37223 607/61 |
| 2011/0190694 | A1 * | 8/2011 | Lanier, Jr. | A61M 5/16881 604/67 |
| 2011/0196337 | A1 * | 8/2011 | Brandt | A61P 3/10 604/151 |
| 2011/0221583 | A1 * | 9/2011 | Yodfat | A61M 5/14248 340/384.6 |
| 2012/0245515 | A1 * | 9/2012 | Calasso | A61M 5/50 604/67 |

FOREIGN PATENT DOCUMENTS

| | | | |
|---|---|---|---|
| WO | | 2005018708 A2 | 3/2005 |
| WO | WO | 2005018708 | 3/2005 |
| WO | | 2006114297 A1 | 11/2006 |
| WO | WO | 2006114297 | 11/2006 |
| WO | | 2007074363 A2 | 7/2007 |
| WO | WO | 2007074363 | 7/2007 |

* cited by examiner

SYSTEM AND METHODS FOR MEDICAMENT INFUSION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

*This application is a reissue application of U.S. patent application Ser. No. 13/139,843, having a 371 completion date of May 24, 2012, now issued U.S. Pat. No. 10,188,788, issued Jan. 29, 2019, which is a U.S. National Stage application, and claims priority of International Application No. PCT/CH2009/000411, filed Dec. 24, 2009, which claims priority of International Application No. PCT/CH2008/000550, filed Dec. 24, 2008.*

The present invention relates to a system for trans-dermal delivery of doses of a medicament comprising a delivery device to be placed in dermal contact with a patient and methods of activating said delivery device by a separate drive device.

BACKGROUND OF THE INVENTION

Many medical conditions often require the regular administration of doses of medicaments. These medicaments are often provided as liquid solutions to be administered intravenously or trans-dermally. Diabetic patients, for example, may require several injections of insulin every day. Patients with chronic diseases may require frequent doses of a pain drug, etc. . . . Mostly, injection pen devices are used by these patients, because they allow an easier and more convenient administration of doses of medicament than with standard syringe and vial. Pen devices however require complex manipulations too, e.g. assembling a new needle every time, replacing a medicament vial when empty, and force the patient to make a new injection every time. This may cause various problems like possible contamination, uncomfortable and embarrassing situation in public place, sore body parts due to multiple injection points. In the attempt to make the life of these patients easier, infusion devices have been developed. The infusion devices known in the art typically comprise a storage device, such as a cartridge, a syringe, a reservoir, containing the liquid medicament, and use electromechanical pumping to deliver the medicament to the patient via tubing to a needle that is inserted through the skin. They typically comprise also all the elements needed for operation and control, e.g. a processor, electric components, a battery, buttons or switches located on the housing of the device, visual feedback via text or graphic screens, such as LCDs, etc. . . . Such devices can be worn in a harness or pocket or strapped to the body of the patient. Currently available infusion devices are expensive, difficult to program and use and tend to be bulky and heavy. Filling these devices can be difficult and require specialized care, maintenance, and cleaning to assure proper functionality and safety for their intended long-term use. In U.S. Pat. No. 6,740,059 an infusion device is disclosed comprising an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. This infusion device is provided with a housing that is free of user input components, such as a keypad or visual screen as these features have been transferred to a separate remote device thus reducing size and complexity of the infusion device. The infusion device, however, still retains all the electro-mechanical components, such as a driving motor, a processor, a battery, and since it needs to be replaced after a few days, appears to be a very expensive disposable.

In WO 02/068015 a system for the continuous delivery of a medicament is disclosed, the system including a disposable assembly having an exit port assembly and a metering portion of a dispenser for controlling fluid flow to the exit port assembly, and a reusable assembly having a control portion of the dispenser adapted to control the metering portion of the dispenser upon attachment of the reusable assembly and the disposable assembly, a local processor connected to the dispenser and programmed to cause fluid flow to the exit port assembly through the dispenser based upon flow instructions, and a local wireless communication element connected to the local processor for receiving flow instructions from a remote wireless device. The assemblies are adapted to be removably attached, and a power source is contained in the disposable assembly for providing power to the reusable assembly upon attachment of the reusable assembly and the disposable assembly. Thus the system disclosed in WO 02/068015 has three components, one disposable, one reusable, which has to be attached to and be in physical contact with the disposable component for the duration of use of the disposable in order to work, and a wireless component to send instructions to the reusable component, which in turn controls the disposable component. Such a system is not only complex and difficult to use, but is still expensive because three system components are needed while the disposable component still retains electromechanical elements such as a battery source and/or complex pumping mechanisms which prevent it to be compact, light, discrete, simple and inexpensive. Moreover, especially in case the system is adapted to deliver doses of medicament rather than for continuous delivery, it is unsafe and unsecure to use since it may be susceptible to external interferences, such as when in the presence of strong electromagnetic fields.

WO 2005/018708 discloses a magnetically coupled implantable actuation system utilizing a magnetically-coupled drive mechanism configured to generate power for implantable medical devices. One variation comprises a drive magnet having a first radius and adapted to rotate about a longitudinal axis when urged, and a driven magnet defining a second radius, which is less than the first radius. This driven magnet is adapted to be implanted within a body and rotate about the longitudinal axis when coaxially positioned within a receiving cavity defined by the drive magnet such that magnetic coupling occurs circumferentially between the driven magnet and the drive magnet. An optional anchor can be used to secure the implanted driven magnet housing against any rotational forces or moments by securing the housing within the subcutaneous layer. This system is however very unsafe and unsecure since it is susceptible to external interferences, such as when in the presence of strong electromagnetic fields, which may cause rotation of the driven magnet and thus lead to unwanted delivery of medicament.

An object of the present invention is to solve some of the problems encountered in the prior art, particularly to provide a cheap device for the delivery of doses of a medicament on a bolus basis. This is achieved by providing a system comprising a delivery device, which is small, comprises a minimum number of components, is easily manufactured, is thus cost-effective and may be disposable. Another advantage of the present invention is that the system is easy and convenient to use. It allows for example easy activation by another person taking care of a patient, a typical situation encountered e.g. when the patient is a child, with elderly people, with temporarily or permanently impaired patients. This is possible because, the present invention enables nearly unnoticed and thus discrete administration of a medicament, and eliminates the need, the fear, the pain, and all problems caused by multiple and repeated injections. Another object of the present invention is to provide a system, which is safe to use and secure against possible interferences. This is achieved by means of a control unit, which can be activated only in a specific manner and thus eliminates the risk that medicament is pumped when not required.

GENERAL DESCRIPTION OF THE INVENTION

The present invention refers to a system for trans-dermal delivery of doses of a medicament, comprising a delivery device to be placed in dermal contact with a patient, the delivery device comprising a reservoir for holding a medicament to be delivered, a trans-dermal injection element for delivering doses of the medicament to the patient, a control unit to control the way an energy external to the delivery device is transformed into pumping force and to guarantee that the correct dose of medicament is pumped and only when a dose is requested. The control unit comprises one or more rotors and/or one or more axial pump elements for transforming rotational and/or axial force into pumping force, and at least one safe-lock mechanism preventing any one or more of the rotors to rotate and/or axial pump elements to move or otherwise preventing the passage of medicament from the reservoir to the trans-dermal injection device until a dose is to be delivered. The system further comprises a separate hand-held drive device to be temporarily placed in proximity of the delivery device only when a dose of medicament is required, the drive device comprising an activation unit for activating the control unit of the delivery device, the activation unit comprising at least one unlocking element to provide energy for unlocking the at least one safe-lock mechanism and a drive unit to provide energy for any one or more of the rotors and/or axial pump elements of the control unit.

A delivery device according to the present invention is a medical unit, which is adapted to deliver trans-dermally to a user multiple doses of a medicament without the need of multiple injections. A typical example of user is a diabetic patient requiring frequent doses of insulin, e.g. in correspondence of each meal. According to a preferred embodiment the delivery device is placed, at least partially, in dermal contact with the user, e.g. removably fixed by means of an adhesive base to the skin of the patient.

The delivery device comprises a reservoir for holding a volume of the medicament to be delivered which is sufficient for several doses. Typically, the delivery device is replaced after a period of time, e.g. 1 to 7 days, typically 2 to 4 days, after several doses of the medicament have been delivered and the reservoir is nearly empty. The reservoir may be of any type, e.g. a syringe or syringe-like, a collapsible pouch, a coiled tube, and may be either pre-loaded with the medicament according to a preferred embodiment or loaded by the patient just before use. According to one embodiment, the reservoir comprises a series or array of chambers, pockets, blisters or pouches disposed on a substrate, e.g. a plate or microfluidic device, wherein each chamber, pocket, blister or pouch contains e.g. a dose or a fraction of dose of medicament to be delivered and is connected by microfluidic channels or tubes to a trans-dermal injection element.

According to one embodiment the delivery device comprises a base rotor for holding the reservoir, so that the reservoir is capable of rotating, at least partially, e.g. when a new dose is required.

The delivery device comprises a trans-dermal injection member, which is adapted to penetrate at least partially the skin of the patient and remain in a trans-dermal position for the duration of use of the delivery device. The trans-dermal injection member is preferably a thin needle, inserted at a controlled depth, but it may be a canula, a catheter, or other form of hollow fluid transport means, inserted e.g. via a removable needle, and adapted to deliver trans-dermally doses of a medicament. More than one, e.g. an array of trans-dermal injection members, is also possible.

The delivery device may further comprise a pump for pumping the medicament from the reservoir to the transdermal injection element and thus through the trans-dermal injection element to the patient. The pump may be any sort of pump, e.g. a pouch pump, a peristaltic pump, a membrane pump, a micropump, as known in the art, adapted for trans-dermal delivery of a medicament. Examples of suitable pumps are disclosed e.g. in U.S. Pat. No. 5,827,219 and WO2007074363.

According to a preferred embodiment, the delivery device comprises at least one pump rotor transforming rotational force into pumping force when rotating around an axis. The pump rotor may be a rod or pin-like element. It may be connected to the pump if present, e.g. directly inserted into the pump or have the form of a disc or the like directly attached to the pump or connected to it, e.g. via a gear mechanism.

According to another preferred embodiment, the delivery device comprises at least one axial pump element transforming axial force into pumping force. The axial pump element may be a plunger-like, a screw-like or any push or pull element, as well as any adapter coupled to a push element, applying axial force. The axial pump element may be directly attached to the pump, if present, or connected to the pump, e.g. adapted to apply axial force on another element of the pump. According to a preferred embodiment the axial pump element is adapted to apply axial force on the liquid contained in the reservoir, the reservoir being e.g. a syringe or a compressible chamber, pouch, pocket, blister, tube, coil or the like.

The axial pump element may move in alternate directions along an axis. In applying the axial force, the axial pump element may vibrate or oscillate, i.e. the axial force may be vibrational or oscillatory. According to one embodiment the axial pump element is a membrane. According to one embodiment the pump is a membrane pump. According to another embodiment the axial pump element comprises a piezo element.

According to the present invention the delivery device comprises a control unit. The term control unit refers to a mechanism, preferably a non-electronic mechanism, which prevents the medicament to be delivered, e.g. to pass from the reservoir to the trans-dermal injection element, until this mechanism is activated in a secure manner by receiving from outside the delivery device the correct amount and form of energy required. Thus the control unit has the function to control the way any force, e.g. rotational force or axial force, is transformed into pumping force when activated and to guarantee that the correct dose of medicament is pumped and only when a dose is requested.

According to a preferred embodiment the control unit comprises at least one primary rotor transferring rotational force to the at least one pump rotor, e.g. via a gear mechanism, a spring mechanism, a belt mechanism.

According to a preferred embodiment the primary rotor and the pump rotor have the same axis of rotation, i.e. they are concentrically arranged, but they might have also different axis, e.g. parallel or orthogonal between them.

A primary rotor may have the function e.g. to change the magnitude of the torque on the pump rotor and/or to minimize the moment of tilt of the pump rotor, that is to minimize inclinations of the axis, which may otherwise cause e.g. leakage, incorrect dosage, more friction, etc. . . .

The control unit may further comprise at least one secondary rotor transferring rotational force to the at least one primary rotor, e.g. via a gear mechanism or spring mechanism.

According to a preferred embodiment, the secondary rotor and the primary rotor have the same axis of rotation, i.e. they are concentrically arranged, but they might have also different axis, e.g. parallel or orthogonal between them.

A secondary rotor may have the same function as a primary rotor.

The control unit may comprise a spring located between the pump rotor and the primary rotor or between the primary rotor and the secondary rotor. According to a preferred embodiment the spring is a mainspring.

One or more axial pump elements may be connected to one or more of the rotors selected from the group of base rotor, pump rotor, primary rotor, secondary rotor, or any other rotor, so that rotational force may be transformed into axial force and vice versa.

Also, an axial pump element may rotate before and/or during and/or after movement in axial direction. Analogously, a rotor may move in axial direction before and/or during and/or after rotation. This means that a rotor may also work as an axial pump element and an axial pump element may also work as a rotor.

The term rotation is used here generically to indicate any number of revolutions or fractions of a revolution without limit of time. Also, rotation may occur in opposite or alternate directions, with constant motion, accelerated motion, or pulse.

According to a preferred embodiment the reservoir for holding the medicament to be delivered is a syringe type reservoir comprising a first end and at least one opening in correspondence of said first end for pumping medicament to the trans-dermal injection element and/or for introducing the medicament in the syringe, a second open end, and walls between said first end and said second end into which a first axial pump element fits in a fluid tight manner. A syringe may be intended also as a tube of any length and shape.

The control unit may advantageously comprise a second axial pump element aligned with said syringe in correspondence of said second open end wherein the first axial pump element is adapted to move towards said second axial pump element when the medicament is being introduced into the syringe.

The second axial pump element may transfer axial force to the first axial pump element after the second axial pump element has come into contact or has engaged with the first axial pump element, that is by pushing the first axial pump element towards the first end of the syringe thus causing pumping of medicament to the trans-dermal injection element. This embodiment may be advantageous for filling the syringe because the first axial pump element is maintained separated from the second axial pump element, thus limiting the function of the second axial pump element only to push for pumping medicament out of the syringe.

According to another embodiment the second axial pump element is a wire attached to the first axial pump element for pulling the first axial pump element towards the first end of the syringe when a dose of medicament is to be delivered. For example the wire may be adapted to slide through one opening in correspondence of the first end of the syringe in a leakage tight manner, e.g. pulling through a septum-like sealing. The wire may be pulled e.g. by coiling around a rotating rotor.

This embodiment may be advantageous for space optimization, e.g. if the syringe is embodied like a longer flexible tube.

According to a preferred embodiment the control unit comprises at least one directional element, allowing any one or more of the rotors selected from the group of base rotor, pump rotor, primary rotor, secondary rotor, to rotate in a preferred direction, and/or one or more axial pump elements to move in a preferred direction. The directional element may be for example an inclined flexible elastic tongue or palette made e.g. of a plastic or metallic material, fitting e.g. between the teeth or grooves of a saw-like or screw-like edge of any rotor or axial pump element.

According to a preferred embodiment any one or more of the elements selected from the group of base rotor, pump rotor, primary rotor, secondary rotor, axial pump element, comprises at least one magnet or a ferromagnetic element.

The magnet may be for example a permanent magnet or a combination of different permanent magnets arranged e.g. to form a specific magnetic configuration.

According to a preferred embodiment the control unit comprises at least one stabilization element for minimizing the moment of tilt, that is to minimize inclinations of the axis, of any one or more of the elements selected from the group of base rotor, pump rotor, primary rotor, secondary rotor, axial pump element, while still rotation and/or movement in the axial direction is allowed. The stabilization element may be for example a primary rotor concentrically arranged with respect to a pump rotor wherein the primary rotor is allowed to incline its axis within a tolerance range without causing an inclination of the axis of the pump rotor. The stabilization element or part of the stabilization element may be also a carved compartment or chamber so designed to fit the outer dimensions or footprint of any one or more elements selected from the group of base rotor, pump rotor, primary rotor, secondary rotor, axial pump element. According to another embodiment the stabilization element may have the form of a cavity or groove into which a part, e.g. a pin, extending from any one or more of the elements selected from the group of base rotor, pump rotor, primary rotor, secondary rotor, axial pump element, may fit. Alternatively the cavity may be on any one or more of the rotors or axial pump elements and into which a stabilization element, e.g. a pin on the inner housing of the housing of the delivery device fits.

According to the invention, the control unit comprises at least one safe-lock mechanism preventing any one or more elements selected from the group of a base rotor, a pump rotor, a primary rotor, a secondary rotor, to rotate, and/or any one or more axial pump elements to move in any direction, until unlocked. Alternatively, the safe lock mechanism may exercise a pressure on or differently occlude the passage of medicament from the reservoir to the trans-dermal injection device until unlocked. The safe-lock mechanism thus eliminates the risk that medicament is pumped when not required, e.g. due to possible interferences.

The safe-lock mechanism may be for example in the form of an insertable/retractable rod or finger or an L-shaped or comb-shaped pivotable arm with one or more teeth, designed e.g. as a clamp, which can assume either of two positions, an engaged or tight position when it is in a locked status and a retracted or enlarged position when it is in an unlocked status. The safe-lock mechanism may be made e.g. of a plastic or metallic material, designed to fit e.g. between the teeth of a saw-like or screw-like edge or cavity at the edges of any rotor or axial pump element, and may comprise a spring, e.g. to return to the locked status after being unlocked, or it may be itself flexible or elastic, e.g. capable of being stretched and to return to its original position afterwards.

According to a preferred embodiment, the safe-lock mechanism is represented by an axial pump element or a rotor e.g. a primary rotor, which needs to move in axial direction and engage with e.g. a pump rotor before rotational force can be transferred to the pump rotor and hence transformed into pumping force.

Alternatively, the pump rotor itself may need to be pushed or pulled in the axial direction before freedom to rotate is provided.

According to a preferred embodiment the at least one safe-lock mechanism comprises at least one ferromagnetic element or a magnet or a coil. The magnet may be for example a permanent magnet or a combination of different permanent magnets arranged e.g. to form a specific magnetic configuration, so that for example only a specific corresponding magnetic field can be used to unlock the safe-lock mechanism.

The present invention thus also refers to a safe-lock mechanism for preventing medicament being delivered from a delivery device wherein the safe lock mechanism is adapted to lock one or more rotors and/or axial pump elements, or otherwise preventing the passage of medicament from the reservoir to the trans-dermal injection device until a dose is to be delivered, and to be unlocked specifically by an unlocking element comprised in a hand-held device to be temporarily placed in proximity of the delivery device, the safe-lock mechanism comprising a coil or at least one magnet or a combination of different magnets arranged to form a specific magnetic configuration and the unlocking element inducing a specific current in the coil or providing a specific magnetic field to unlock the safe-lock mechanism.

In order to deliver a dose of medicament the control unit needs to be activated. Activating the control unit means unlocking one or more safe-lock mechanisms. Activating the control unit means also transferring rotational force to at least one rotor, e.g. a base rotor, a pump rotor, a primary rotor, a secondary rotor and/or axial force to at least one axial pump element comprised in the delivery device without an energy source being present in the delivery device itself. The energy source required to activate the control unit comes from a separate hand-held drive device to be temporarily placed in proximity of the delivery device when a dose of medicament is required, the drive device comprising an activation unit. The activation unit enables to deliver a dose of medicament when it is requested by providing the correct amount and form of energy to the control unit. Particularly, the unlocking element may unlock the safe-lock mechanism in a specific manner as a key and/or the unlocking element and the drive unit may cooperate synergistically to activate the control unit in a specific manner as a key.

Thus all or most electronic components, such as e.g. a processor, a memory, switch and operational buttons, electric circuits, printed circuit board, wires, a visual and/or Braille-like display, a battery or other form of power supply, one or more ports for recharging and/or for connecting to other devices, e.g. a computer, e.g. for exchanging data, alert or warning lights and audio or vibration signals and alarms, e.g. to inform the user that the dose has been delivered and the hand-held device can be removed, or that an atypical situation has been encountered, may be integrated on the separate hand-held drive device rather than on the delivery device, which remains preferably as simple as possible. The drive device may advantageously comprise a feedback system, e.g. a receiver, capable of receiving information from the delivery device, e.g. a signal confirming that the correct amount and form of energy has been transferred and/or that the correct dose of medicament has been delivered and/or that an atypical situation has been encountered, e.g. a clogging or when the reservoir is empty. The feedback signal may be for example, electromagnetic, e.g. generated by the movement of magnets or by a coil in the delivery device, or acoustic, e.g. a noise generated, in the delivery device. According to a preferred embodiment the drive device comprises a sensor capable of receiving feedback signals from the delivery device, i.e. capable of detecting the amount of energy being transferred and/or transformed into pumping force and/or medicament delivery. According to a preferred embodiment the sensor is a Hall Sensor. Identification means such as an RFID chip may also be integrated on the delivery device for being identified by the hand-held drive device. The chip may be used to verify that correct delivery device is being activated by the drive device and/or may be adapted to send a feedback signal, e.g. when the reservoir is empty, for example by being contacted directly or indirectly by a moving axial pump element.

According to a preferred embodiment the activation unit comprises at least one unlocking element for unlocking the at least one safe-lock mechanism of the control unit when the hand-held drive device is placed in proximity of the delivery device.

According to a preferred embodiment the unlocking element comprises at least one magnet. The magnet may be for example a permanent magnet or a combination of different permanent magnets, or an electromagnet, e.g. a coil capable of generating a magnetic field, which interacts with the at least one ferromagnetic element or magnet or coil comprised in the safe-lock mechanism. Such interaction between magnetic field generated by the unlocking element and magnet or magnets or coils comprised in the safe-lock mechanism may be specific, or modulated, meaning that only in presence of the magnetic field generated by the unlocking element and only at a certain distance the safe-lock mechanism can be unlocked as with a key, while it remains in the locked status in the presence of any other magnetic field which may be encountered in the environment. This specific activation may thus introduce a further safety measure in the use of the delivery device.

According to a preferred embodiment the activation unit comprises a drive unit providing rotational force and/or axial force to any one or more elements selected from the group of a base rotor, a pump rotor, a primary rotor, a secondary rotor, axial pump element when the hand-held drive device is placed in proximity of the delivery device.

The drive unit may comprise electromagnets or a drive rotor or a drive element connected to a motor, the drive rotor or drive element comprising at least one magnet. The magnet may be for example a permanent magnet or a combination of different permanent magnets arranged e.g. to generate a specific magnetic field.

According to a preferred embodiment the separate hand-held drive device in correspondence of the activation unit is shaped as to form a complementary cavity into which at least a part of the delivery device comprising the control unit substantially fits. The term substantially here refers to a tolerance range in which activation is still possible while at the same time leaving enough space e.g. for one or more layers of clothing to be sandwiched in between.

According to another embodiment electrical contact is established between the drive device and the delivery device or between the activation unit and the control unit. Thus energy may be transferred from the drive device to the delivery device in the form of current via contact. Alternatively a current may be induced in the delivery device by the drive device. The delivery device may comprise e.g. coils or transformers, capable of generating current when exposed to a magnetic field generated by the activation unit. The induced electrical power may be used e.g. to transform rotational force and/or axial force into pumping force and/or to unlock the safe-lock mechanism and/or to generate a feedback signal.

According to another embodiment the delivery device comprise a capacitor or accumulator for receiving and/or accumulating energy from the drive unit when the drive unit is placed in proximity of the delivery device. This energy may be used by the control unit e.g. after the drive device has been removed.

The present invention also refers to a safe-lock mechanism for preventing medicament being delivered from a delivery device wherein the safe-lock mechanism is adapted to lock one or more rotors and/or axial pump elements and to be unlocked specifically by an unlocking element comprised in a hand-held device to be temporarily placed in proximity of the delivery device, the safe-lock mechanism comprising a coil or at least one magnet or a combination of different magnets arranged to form a specific magnetic configuration and the unlocking element inducing a specific current in the coil or providing a specific magnetic field to be used to unlock the safe-lock mechanism.

The present invention also refers to a method of activating the control unit comprising any one or more of the following steps:

- unlocking a safe-lock mechanism in the control unit, by means of an unlocking element comprised in the activation unit,
- providing energy to be transformed into rotational force and/or axial force for any one or more elements selected from the group of a base rotor, a pump rotor, a primary rotor, a secondary rotor, axial pump element, by means of a drive unit comprised in the activation unit,
- loading a spring, located between a pump rotor and a primary rotor or between a primary rotor and a secondary rotor, by providing rotational force to either the primary rotor or the secondary rotor respectively,
- allowing the spring to return to a previous status while causing rotation of the pump rotor either directly or via rotation of the primary rotor.

More in detail the present invention is explained with reference to the following drawings representing schematically favorite embodiments where like numbers refer to like features.

DETAILED DESCRIPTION OF THE INVENTION

Figure 1A:
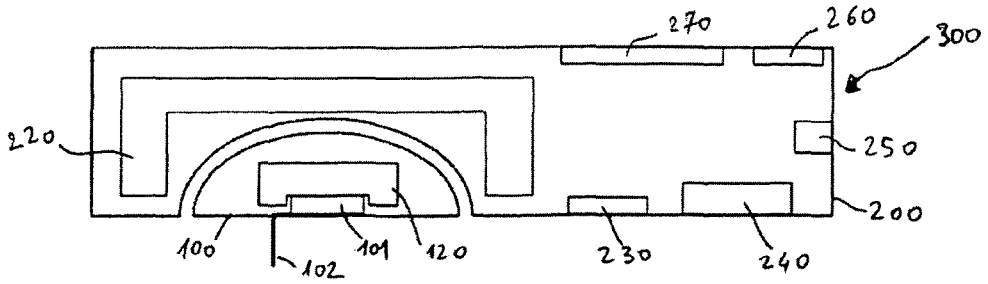
FIG. 1a shows a system comprising a delivery device and a separate drive device temporarily placed in proximity of the delivery device.

FIG. 1a shows a system 300 for trans-dermal delivery of doses of a medicament, comprising a delivery device 100 to be placed in dermal contact with a patient. The delivery device 100 comprises a reservoir 101 for holding a medicament to be delivered, a trans-dermal injection element 102 for delivering doses of the medicament to the patient, a control unit 120 for controlling the delivery of the medicament when activated. The system 300 further comprises a separate hand-held drive device 200 temporarily placed in proximity of the delivery device 100, the drive device 200 comprising an activation unit 220 for activating the control unit 120 of the delivery device 100. The drive device 200 in correspondence of the activation unit 220 is shaped as to form a complementary cavity 221 into which the delivery device 100 comprising the control unit 120 substantially fits. The drive device 200 further comprises all the elements needed for operation and control, e.g. a processor 230, other electronic components (not shown) such as a memory, a printed circuit board, wires, etc. . . . a battery 240, a port 250 for recharging and/or for connecting to other devices, e.g. a computer, e.g. for exchanging data, buttons or switches 260 located on the housing of the device, visual and/or Braille-like screens, e.g. an LCD 270, alert or warning lights (not shown).

Figure 1B:
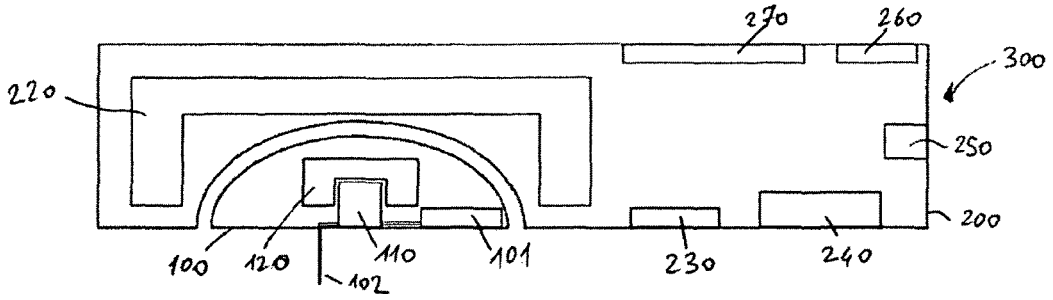
FIG. 1b shows a variant of FIG. 1a wherein the delivery device comprises also a pump.

FIG. 1b is the same as FIG. 1a except that the delivery device 100 further comprises a pump 110 for pumping the medicament from the reservoir 101 to the trans-dermal injection element 102.

Figure 2:
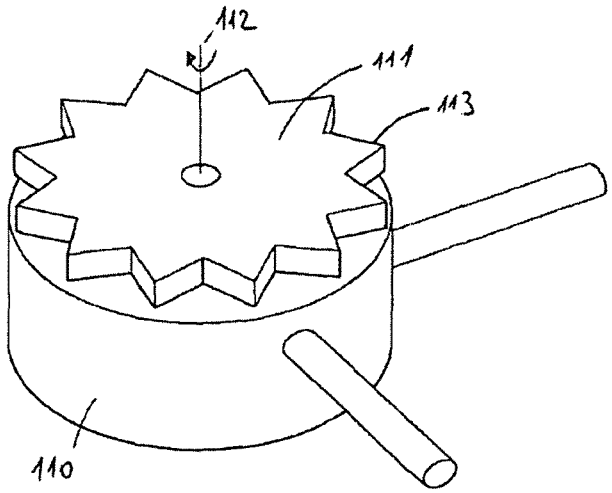
FIG. 2 shows a pump rotor connected to the pump inside the delivery device.

FIG. 2 shows a pump rotor 111 connected to the pump 110 located in the delivery device 100 transforming rotational force into pumping force when rotating around an axis 112. The pump rotor 111 presents a saw-like or gear-like edge 113.

FIGS. 3 to 11 depict preferred embodiments of the control unit 120.

Figure 3:
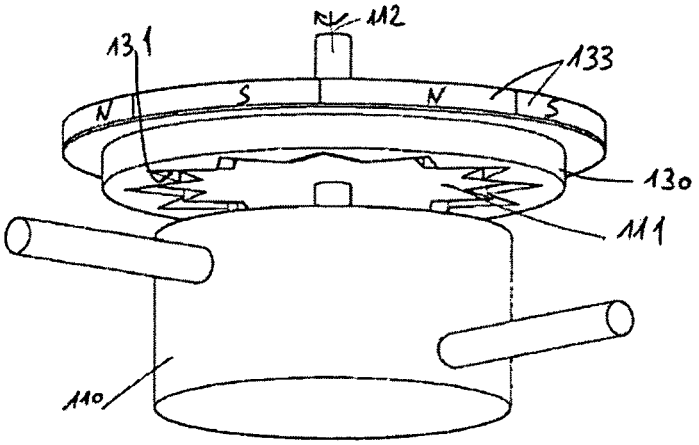
FIG. 3 shows part of a control unit comprising a primary rotor.

FIG. 3 shows a primary rotor 130 connected to the pump rotor 111 via a gear mechanism, adapted to transfer rotational force to the pump rotor 111. The pump rotor 111 fits with a certain tolerance into a cavity 131 at the bottom of the primary rotor 130. The primary rotor 130 and the pump rotor 111 thus have approximately the same axis of rotation 112, i.e. they are concentrically arranged. The primary rotor 130 comprises a pin 132 parallel to the axis of rotation 112, which fits into a cavity (not shown). The primary rotor 130 works as a stabilization element wherein it is allowed to incline its axis within a tolerance range without causing an inclination of the axis of the pump rotor 111. In this way the moment of tilt of the pump rotor is minimized, that is inclinations of the axis 112 during rotation are minimized. The pin 132 could be attached directly to the pump rotor 111. The primary rotor 130 comprises also a series of permanent magnets 133 arranged according to a specific magnetic configuration. Magnets 133 could have been disposed also on the primary rotor 111.

Figure 4:
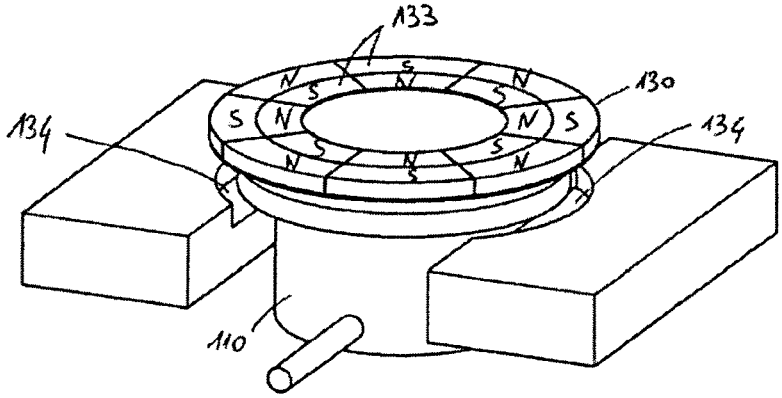
FIG. 4 shows a variant of the embodiment of FIG. 3.

FIG. 4 shows a variant of the embodiment of FIG. 3 wherein a compartment 134 carved in the housing of the delivery device 100 and designed to fit the footprint of the primary rotor 130 is part of the stabilization element. This could be used together with the pin 132.

Figure 5:
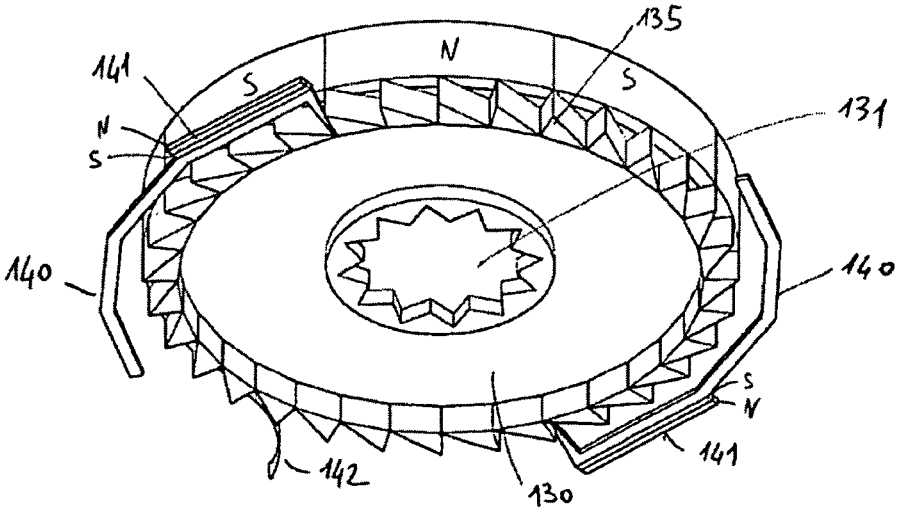
FIG. 5 shows part of a control unit wherein a primary rotor is locked by a safe-lock mechanism.

FIG. 5 shows part of a control unit 120 wherein a primary rotor 130 is locked by a safe-lock mechanism 140. The safe-lock mechanism 140 prevents the primary rotor 130 to rotate until unlocked. The safe-lock mechanism 140 thus eliminates the risk of external interferences, i.e. that medicament is pumped when not required. The safe-lock mechanism 140 has the form of L-shaped pivotable arms, designed as a clamp, which can assume either of two positions, a tight position (as shown in the figure) when it is in a locked status and an enlarged position when it is in an unlocked status (not shown). The safe-lock mechanism 140 is designed to fit at one extremity between the teeth of a saw-like edge 135 of the primary rotor 130 and is made of a rigid but flexible elastic material capable of being stretched and to return to its original position afterwards. The safe-lock mechanism 140 comprises permanent magnets 141. Also shown in FIG. 5 is a directional element 142, which allows the primary rotor 130 to rotate in one direction only when unlocked. The directional element 142 is an inclined flexible elastic tongue fitting between the teeth of the saw-like edge 135 of the primary rotor 130.

Figure 6:
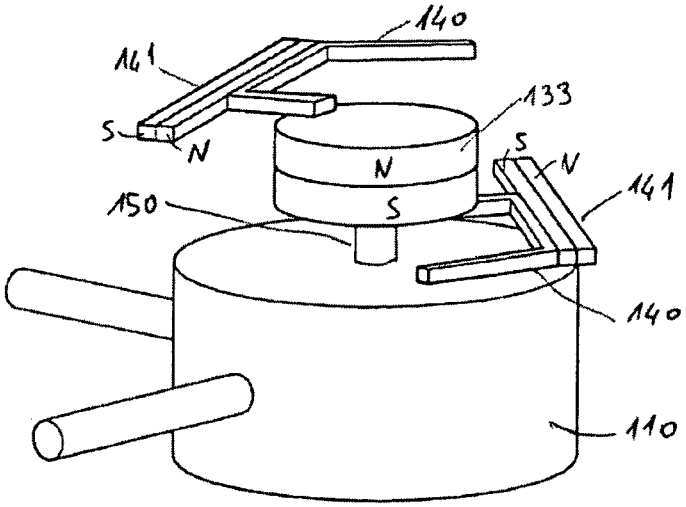
FIG. 6 shows the pump of FIG. 2 connected to an axial pump element locked by a safe-lock mechanism.

FIG. 6 shows the pump 110 connected to an axial pump element 150 locked by a safe-lock mechanism 140. The axial pump element 150 is directly attached to the pump 110 and is adapted to transform axial force into pumping force. Disposed on the axial pump element is a magnet 133. The safe-lock mechanism 140 is similar to that shown in FIG. 5. In this case, it prevents the axial pump element 150 to move up and/or down until unlocked.

Figure 7:
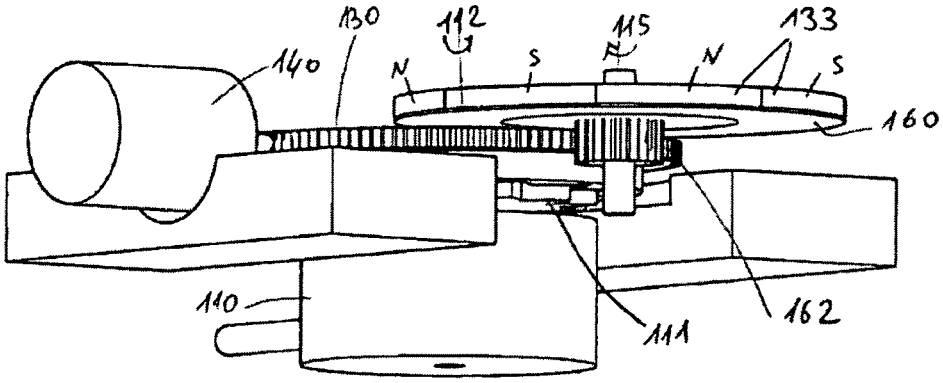
FIG. 7 shows a secondary rotor and a primary rotor having different axis of rotation, the primary rotor being locked by a safe-lock mechanism.

FIG. 7 shows a secondary rotor 160 and a primary rotor 130 having different axis of rotation 115 and 112 respectively, while the primary rotor 130 and the pump rotor 111 have the same axis of rotation 112. The secondary rotor 160 has here the function to change the magnitude of the torque on the primary rotor 130 and hence on the pump rotor 111 by means of a gear mechanism 162. The secondary rotor 160 comprises a series of permanent magnets 133 and is capable of transferring rotational force to the primary rotor 130, which in turn is capable of transferring rotational force to the pump rotor 111. The primary rotor 130 is locked by a safe-lock mechanism 140, which acts as a brake on the primary rotor 130 until unlocked. The safe lock mechanism 140 may be unlocked analogously to FIGS. 5 and 6 magnetically or electronically, e.g. powered by an induced electric current.

Figure 8A:
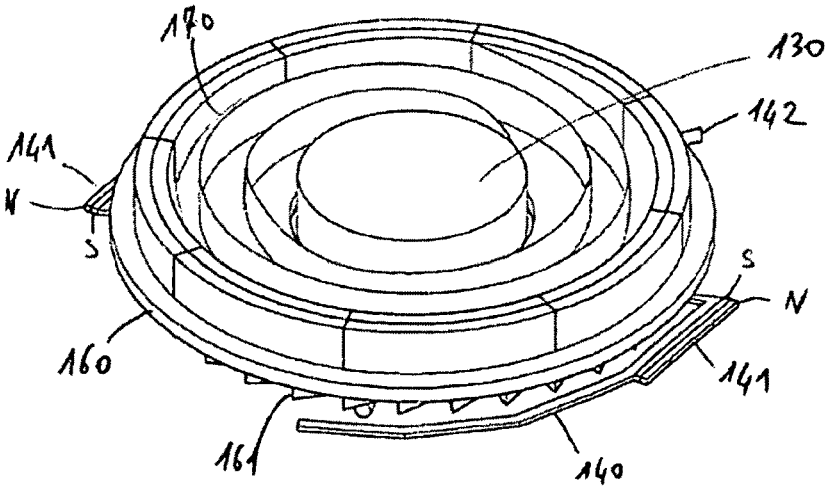
FIG. 8a is a perspective view of an embodiment comprising a spring located between a primary rotor and a secondary rotor.

FIG. 8a is a perspective view of an embodiment comprising a mainspring 170 located between a primary rotor 130 and a secondary rotor 160. The secondary rotor 160 comprises a series of permanent magnets 133 arranged according to a specific magnetic configuration. The secondary rotor 160 is locked by a safe-lock mechanism 140 similar to that shown in FIG. 5. The safe-lock mechanism 140 fits at one extremity between the teeth of a saw-like frame 161 of the secondary rotor 160 and prevents the secondary rotor 160 to rotate until unlocked. A second safe-lock mechanism (not shown) may lock the primary rotor 130 while the secondary rotor 160 is unlocked and allowed to rotate. A directional element 142 allows the secondary rotor 160 to rotate in one direction only when unlocked. Rotation of the secondary rotor 160 in one direction has in this case the function to load the mainspring 170. Once the mainspring 170 is loaded the drive device 200 may be removed as rotational force is transferred now to the primary rotor 130 by the mainspring 170 while returning to its previous status. The mainspring 170 may be differently loaded according to the dose to be delivered.

Figure 8B:
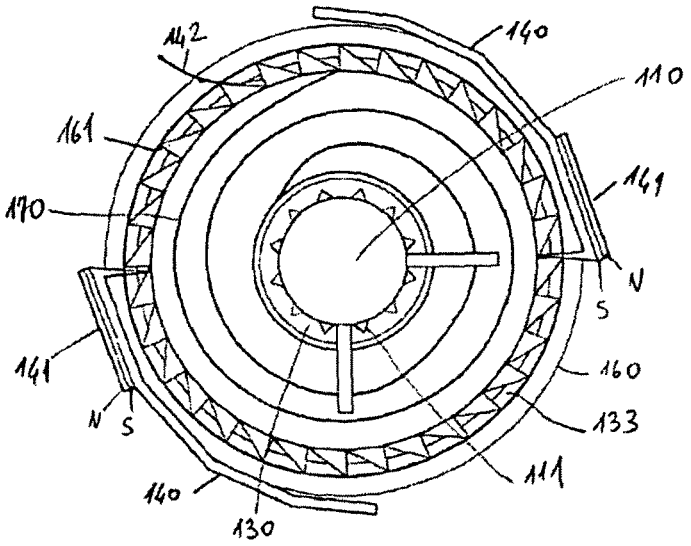
FIG. 8b is a bottom view of the embodiment of FIG. 7.

FIG. 8b is a bottom view of the embodiment of FIG. 8a wherein the secondary rotor 160 has been made transparent for clarity. The pump rotor 111, the primary rotor 130 and the secondary rotor 160 are concentrically arranged with the mainspring 170 located between the secondary rotor 160 and the primary rotor 130. The primary rotor 130 could have been in place of the secondary rotor 130 and the mainspring 170 could have been located between the primary rotor 130 and the pump rotor 111.

Figure 9:
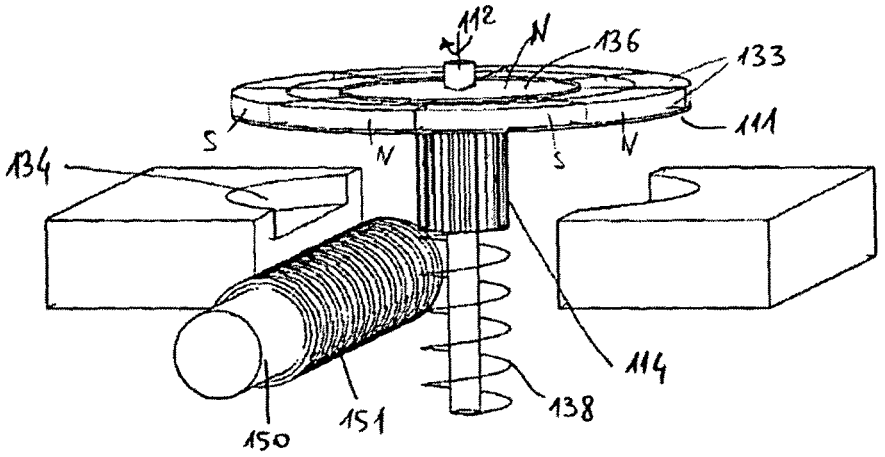
FIG. 9 shows a pump rotor designed to engage with an axial pump element and to transform rotational force into axial force upon activation.

FIG. 9 shows a pump rotor 111 designed to engage with an axial pump element 150 and to transform rotational force into axial force upon activation. The pump rotor 111 and the axial pump element 150 are not connected to each other, i.e. the pump rotor 111 may be allowed to rotate but eventual rotational force applied to the pump rotor 111 is not transferred to the axial pump element 150 and transformed into axial force, until the separate hand-held drive device 200 comprising the activation unit 220 is temporarily placed in proximity of the delivery device 100. Thus the separation of the pump rotor 111 and the axial pump element 150 has the same function of a safe-lock mechanism 140. Unlocking the safe-lock mechanism here means moving the pump rotor 111 in axial direction in order to engage with the axial pump element 150. In particular, a gear element 114 of the pump rotor 111 is engaged with a gear element 151 of the axial pump element 150. The pump rotor 111 comprises a series of permanent magnets 133, 136 arranged according to a specific magnetic configuration. The axial pump element 150 is here the plunger of a syringe-like reservoir (not shown), comprising the medicament to be delivered. A spring 138 allows the pump rotor 111 to disengage and return to its original locked status once the drive device 200 is no longer in proximity of the delivery device 100.

Using a similar mechanism and with reference to FIG. 3 one can imagine a primary rotor 130, which needs to move in the axial direction in order to be engaged with the pump rotor 111.

Figure 10:
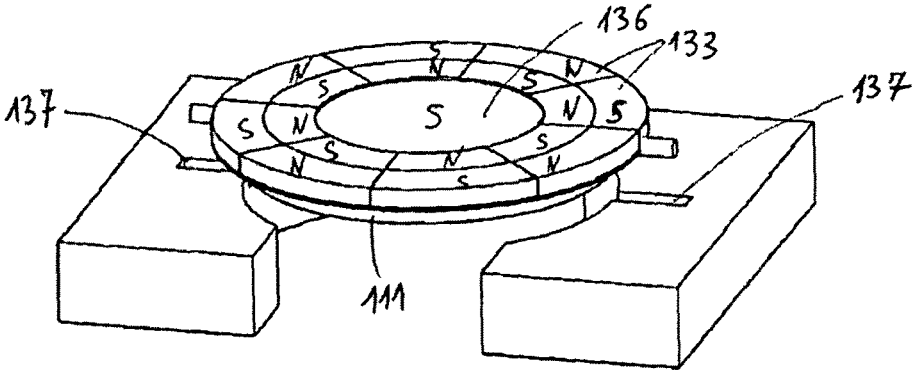
FIG. 10 shows another example wherein the pump rotor needs to move in the axial direction before freedom to rotate is provided.

FIG. 10 shows another example wherein the pump rotor 111 needs to be pulled in the axial direction out of its locked position 137 before freedom to rotate is provided.

Figure 11:
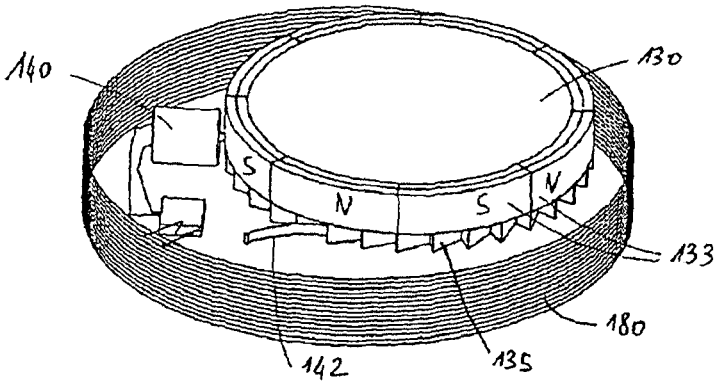
FIG. 11 shows a coil integrated in the delivery device capable of providing induced electrical power for unlocking a safe-lock mechanism.

FIG. 11 shows a coil 180 integrated in the delivery device 100. A specific magnetic field generated by the activation unit 220 when the drive device 200 is placed in proximity of the delivery device 100 induces a specific current, e.g. modulated, in the coil 180, which provides electrical power for unlocking the safe-lock mechanism 140 for a specific period of time.

Figure 12:
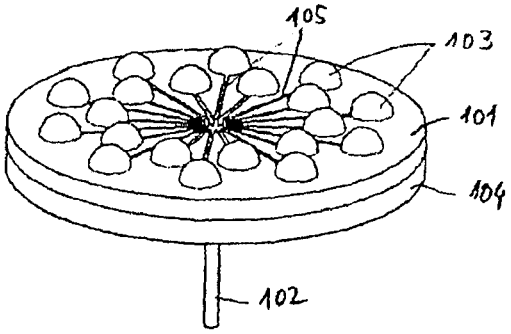
FIG. 12 shows a reservoir comprising an array of blisters disposed on a base rotor.

FIG. 12 shows a reservoir 101 comprising an array of blisters 103 disposed on a base rotor 104, each blister 103 containing a fraction of dose of medicament to be delivered and being connected by a microfluidic channel 105 to the trans-dermal injection element 102. The base rotor 104 is capable of rotating, at least partially when a new dose is required. The control unit comprises a safe-lock mechanism (not shown) preventing the base rotor 104 to rotate until unlocked and an axial pump element (not shown) transforming axial force into pumping force by pressing on the blisters 103 one at a time. Instead of a rotating base rotor 104 a rotating axial pump element (not shown) could be used as well. Instead of an array of blisters 103 a single larger pouch (not shown) could be used as well.

Figure 13:
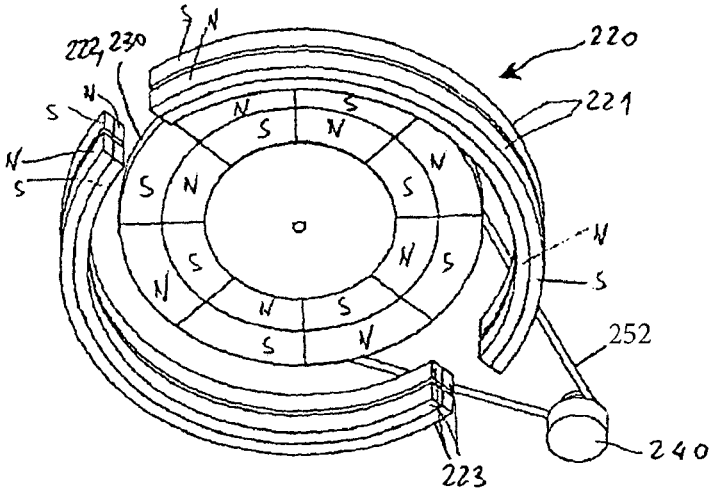
FIG. 13 shows the elements of an activation unit comprised in the drive device.

FIG. 13 shows the elements of an activation unit 220 comprised in the drive device 200. The design of the activation unit 220 may vary in order to adapt to different control units 120. The activation unit 220 of FIG. 13 is for example suitable for a control unit as shown in FIGS. 5 to 8. In particular, the activation unit 220 comprises an unlocking element 221 for unlocking the at least one safe-lock mechanism 140 of the control unit 120 when the hand-held drive device 200 is placed in proximity of the delivery device 100. The unlocking element 221 comprises permanent magnets 223 symmetrically arranged. This symmetry may be convenient in order to avoid dependency on the angle with which the hand-held drive device 200 is placed in proximity of the delivery device 100. An electromagnet could have also been used. The magnetic field generated by the unlocking element 221, which may be specific, is the key for unlocking the safe-lock mechanism 140. The activation unit 220 further comprises a drive unit 222 providing rotational force and/or axial force to any one or more elements selected from the group of a base rotor 104, a pump rotor 111, a primary rotor 130, a secondary rotor 160, an axial pump element 150 when the hand-held drive device 200 is placed in proximity of the delivery device 100. The drive unit 222 comprises a drive rotor 230 connected to a motor 240 via a belt 252, the drive rotor 230 comprising a series of magnets 231. An electromagnet could have also been used.

Figure 14:
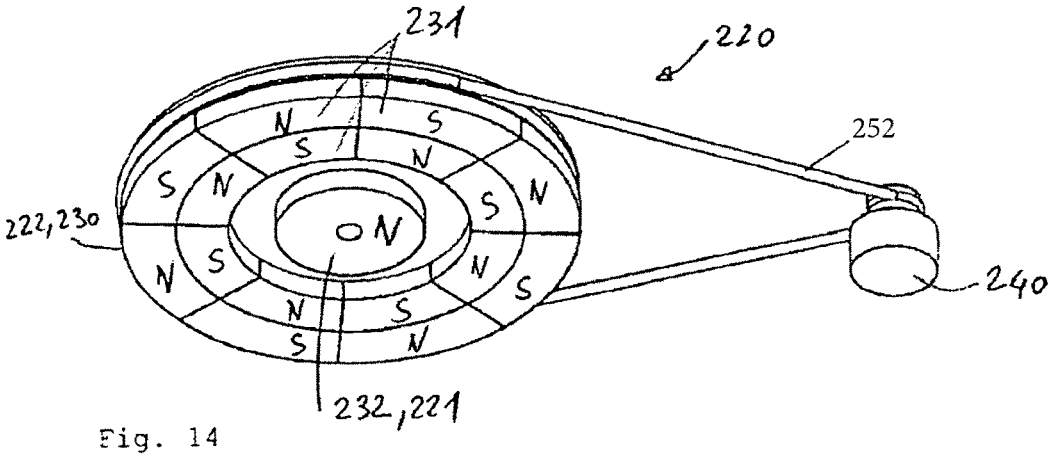
FIG. 14 shows a different embodiment of an activation unit.

FIG. 14 shows a different embodiment of an activation unit 220 wherein the magnets 231 comprised in the drive rotor 230 are differently arranged. The drive rotor 230 comprises also another magnet 232 at the center, which acts as unlocking element 221 for a safe-lock mechanism like that described e.g. in relation to FIGS. 9 and 10.

Figure 15:
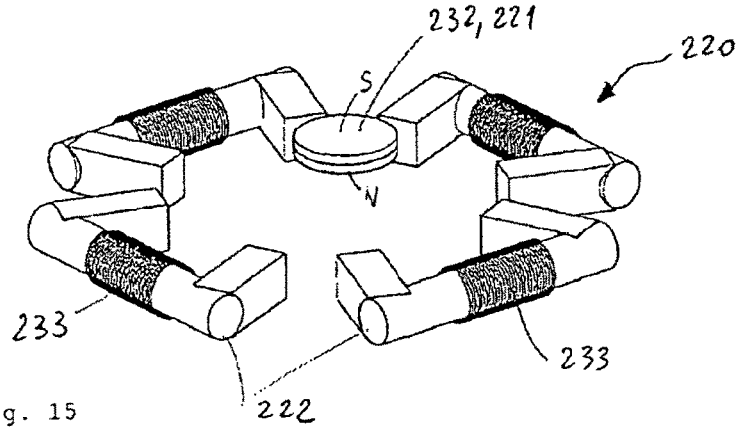
FIG. 15 shows another embodiment of an activation unit.

FIG. 15 shows still another embodiment of an activation unit comprising a magnet 232 at the center and acting as unlocking element 221 similarly to that shown in FIG. 14. As a drive unit 222 a series of electromagnets represented by coils 233 are used instead.

Figure 16:
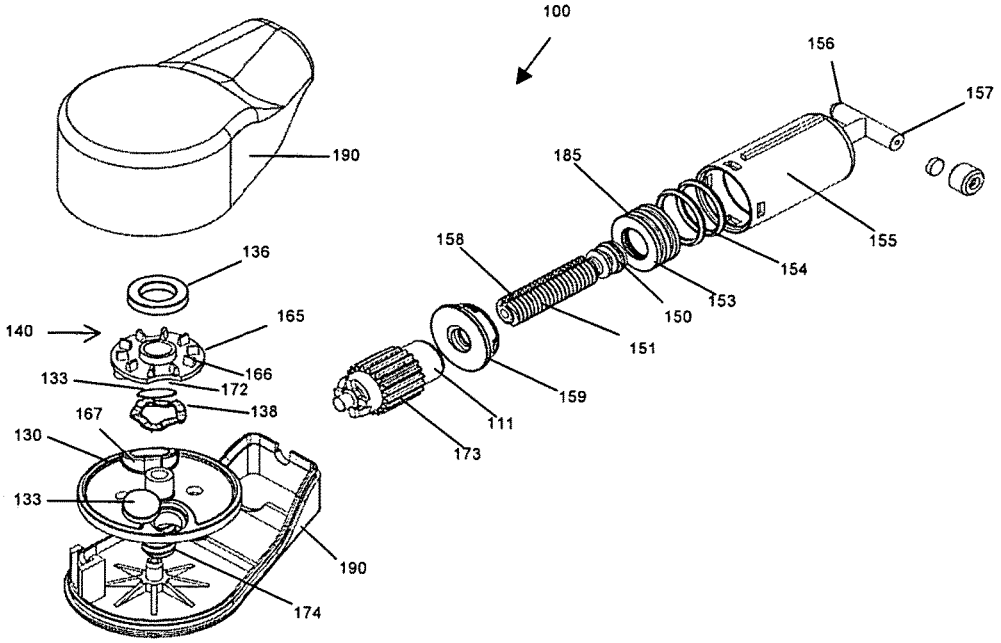
FIG. 16 shows some of the components of a delivery device more in detail in an exploded view.
Figure 17A:
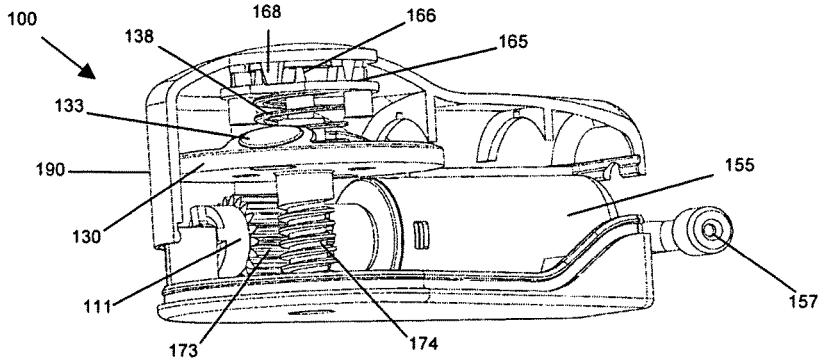
FIG. 17a shows the interaction between some of the elements of the delivery device of FIG. 16 through the housing partially removed for clarity.
Figure 17B:
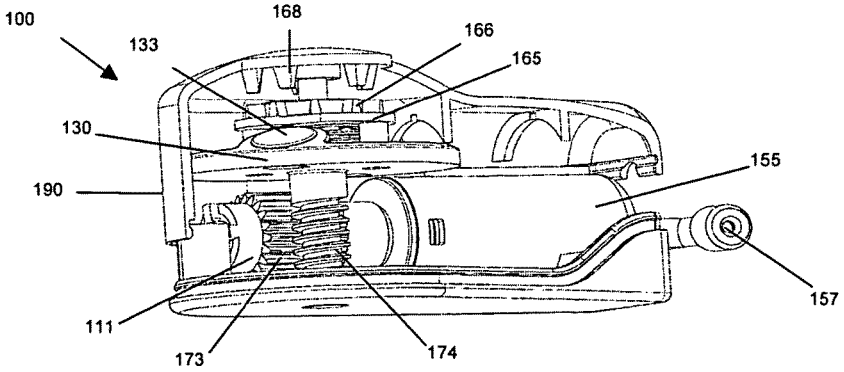
FIG. 17b shows the interaction between some of the elements of the delivery device of FIG. 16 through the housing partially removed for clarity.
Figure 18A:
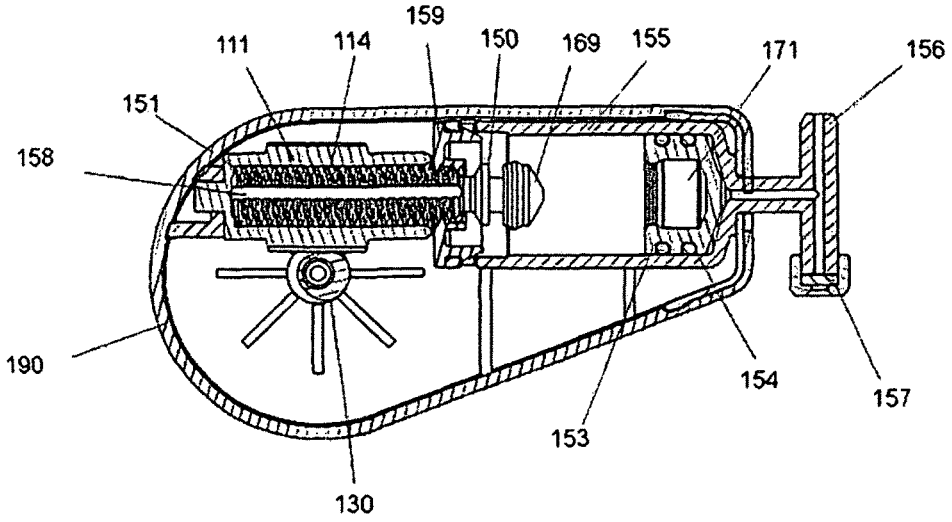
FIG. 18a shows the interaction between some of the elements of the delivery device of FIG. 16 in cross-sectional view.
Figure 18B:
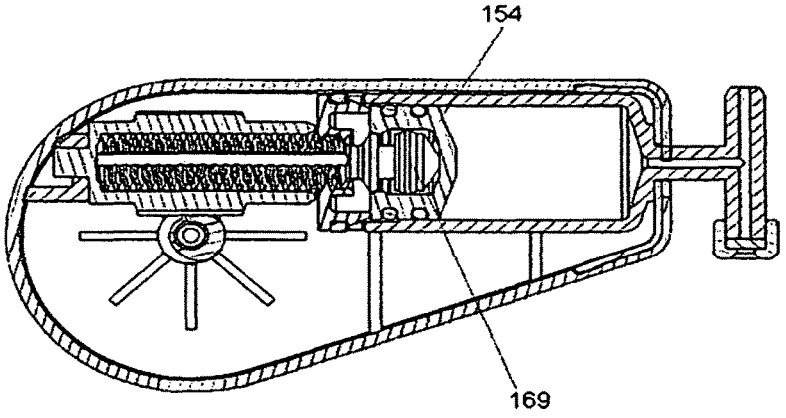
FIG. 18b shows the interaction between some of the elements of the delivery device of FIG. 16 in cross-sectional view.

FIG. 16 to FIG. 18b show the elements of a delivery device 100 according a preferred embodiment and are to be seen together. FIG. 16 is an exploded view showing most of the elements of the delivery device 100. FIG. 17a and FIG. 17b show the interaction between some of the elements of the delivery device 100 of FIG. 16, wherein in FIG. 17a shows the safe-lock mechanism in a locked status and FIG. 17b shows the safe-lock mechanism in an unlocked status. FIG. 18a and FIG. 18b show the interaction between some other elements of the delivery device 100 of FIG. 16 not visible in FIG. 17a and FIG. 17b. The embodiment shown in these figures is similar in principle to that shown in FIG. 9. The reservoir 155 is a syringe for containing the medicament to be delivered. A plunger-like axial pump element consisting of a first axial pump element 153 and a second axial pump element 150 transforms axial force into pumping force for pushing the medicament out of the syringe via opening 157 fluidically connected to trans-dermal injection element 102 (not shown). A second opening 156 may be used, e.g. to introduce the medicament into the syringe 155. The first axial pump element 153 comprises o-rings 154 for achieving a fluid-tight sealing with the inner walls of syringe 155. The first axial pump element 153 is disconnected from the second axial pump element 150 before introducing the medicament into then syringe. Particularly, the first axial pump element 153 is close to a first end of the syringe 155 in proximity of the openings 156, 157 and is pushed towards second axial pump element 150 by the medicament being introduced into the syringe 155, until engaging with the second axial pump element 150 by fitting head 169 of the second axial pump element 150 into cavity 171 of the first axial pump element 153. The syringe 155 is closed at the second open end with a cap 159 secured at the inner walls of the syringe 155 so that it is not allowed to rotate. The cap comprises a hole in the center and a tooth (not shown) protruding towards the center. The second axial pump element 150 may pass through the hole of the cap 159. The second axial pump element 150 comprises a gear element 151 and a groove 158, into which the tooth of the cap 159 fits. In this way the second axial pump element 150 may move axially into the syringe 155 through the hole of the cap 159 but may not rotate, due to the groove 158 being aligned with the tooth of the cap 159. The second axial pump element 150 fits into the body of pump rotor 111 and is connected via the gear element 151 with a first internal gear element 114 of the pump rotor 111. The pump rotor 111 is designed to transform rotational force into axial force by pushing upon rotation the second axial pump element 150 in axial direction, which in turn pushes the first axial pump element 153. A primary rotor 130 is connected via gear element 174 with a second external gear element 173 of the pump rotor 111. The primary rotor 130 is designed to transfer rotational force to pump rotor 111 upon activation.

The pump rotor 111 may rotate and transform rotational force into axial force only if the primary rotor 130 is allowed to rotate. The primary rotor 150 is however locked by a safe-lock mechanism 140 and is not allowed to rotate until a separate hand-held drive device 200 is placed in proximity of the delivery device and only when a dose of medicament is required, the drive device 200 comprising an activation unit 220 for activating the control unit 120 of the delivery device 100, the activation unit 220 comprising an unlocking element 221 to provide energy for unlocking the safe-lock mechanism 140 and a drive unit 222 to provide energy for the primary rotor 130 to rotate.

The safe-lock mechanism 140 comprises a locking element 165 comprising teeth 166. The locking element 165 is designed to be functionally coupled to primary rotor 130 so that primary rotor 130 may rotate only together with locking element 165. This is achieved by matching recesses 172 of the locking element 165 with protrusions 167 on the primary rotor 130. A spring 138 located between the locking element 165 and the primary rotor 130 pushes the locking element 165 against the inner walls of the housing 190 of the delivery device 100, wherein similar protruding teeth 168 prevent the locking element 165 and thus the primary rotor 130 to rotate. A spring 138 like that shown in FIG. 16 may be more suitable than a spring 138 like that shown in FIG. 17a and FIG. 17b. The spring type has been changed in FIG. 17a and FIG. 17b for illustration purpose only, wherein also the distance between the locking element 165 and the primary rotor 130 has been exaggerated for better clarity. During operation, the locking element 165 is normally not allowed to go over the upper level of protrusions 167 on the primary rotor 130. The primary rotor 130 comprises also two permanent magnets 133. Another magnet 136 is placed above the locking element 165.

The safe-lock mechanism 140 comprises in this case the locking element 165 with teeth 166, the spring 138, the magnet 136 and teeth 168 of the housing 190. The control unit 120 comprises the primary rotor 130, the pump rotor 111, the second axial pump element 150, the first axial pump element 153, the cap 159, and the safe-lock mechanism 140.

When a dose of medicament is required a separate hand-held drive device 200 comprising an activation unit 220 similar to that shown in FIG. 14 or FIG. 15 is placed in proximity of the delivery device 100 and a command is given to activate the control unit 120 to delivery specifically the dose of medicament needed. The drive device 200 comprises an activation unit 220 for activating the control unit 120 of the delivery device 100. The activation unit 220 comprises an unlocking element 221, the unlocking element 221 comprising a magnet 232 to interact specifically with magnet 136, so that the magnetic force overcomes the force provided by the spring 138 and the locking element is pushed downwards towards the primary rotor 130, thus freeing the locking element 165 from teeth 168 and unlocking the control unit 120. At the same time the drive unit 222 of the drive device 200, comprising magnets 231 with a specific magnetic configuration matching the polarity of the magnets 133 on the primary rotor 130 provides to the primary rotor 130 the exact amount of energy to rotate, which is transformed via pump rotor 111 into the exact axial force required to deliver the correct dose of medicament. As soon as the requested dose has been delivered, the drive unit 222 stops to provide energy to the primary rotor 130, which stops rotating. The hand-held device sends a feedback signal, e.g. visual, vibrational, acoustic, to inform the user that it is possible to remove the hand-held device 200 from the delivery device 100. The safe-lock mechanism 140 is then locked again, thus locking the control unit 120. The combined effect of the unlocking element 221 and the drive unit 222 on the combined elements of the control unit 120 makes the activation of the control unit 120 specific as a key.

Figure 19:
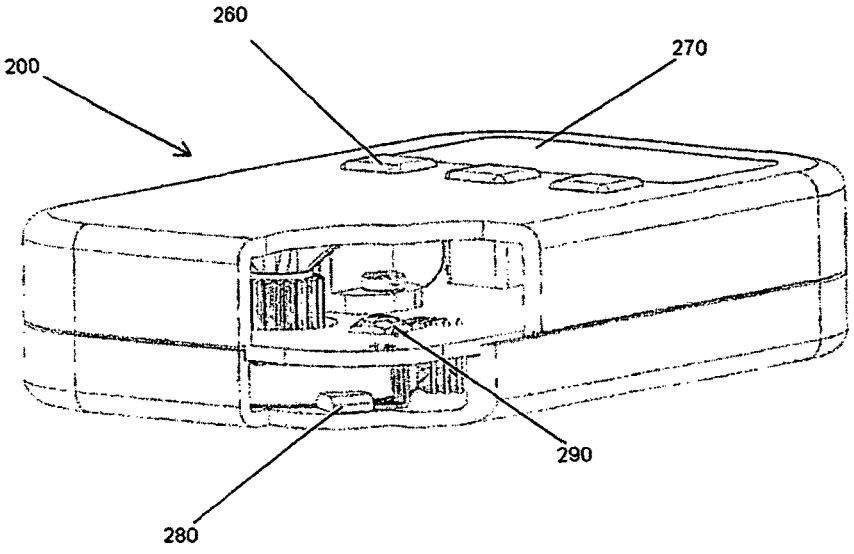
FIG. 19 shows a hand-held drive device wherein part of the housing has been removed to show some of the elements inside.

FIG. 19 shows a hand-held drive device 200 wherein part of the housing has been removed to show some of the elements inside. Particularly a Hall sensor 280 and an encoder 290 are shown. The Hall sensor is capable of detecting the fluctuation of the magnetic field induced by the magnets 133 when the primary rotor 130 rotates and thus enables the verification that the correct amount of energy has been transferred to the control unit 120 and transformed into pumping force and delivery of the correct dose of medicament. In this case, the drive device 200 comprises an activation unit similar to that of FIG. 14 and the encoder 290 is used to verify the rotational movement of the drive unit 222. The data from the hall sensor 280 and the encoder 290 may be compared for further verification.

Of course numerous variations of the described embodiments are possible without departing from the scope of the invention.

The invention claimed is:

1. A *drug delivery* system [for trans-dermal delivery of a dose of a medicament,] comprising*:* a delivery device*;* and a separate [hand-held] drive device, wherein the delivery device [is configured to be placed in dermal contact with a patient, the delivery device comprising] *comprises:* a reservoir for holding [the] *a* medicament [to be delivered,] *and;*

[a trans-dermal injection element for delivering the dose of the medicament to the patient,]

a control unit for controlling the transformation of external energy transferred from the [hand-held] drive device to the delivery device into a pumping force [and for allowing a specific dose of the medicament to be pumped when the dose is requested], the control unit comprising*:*

[one or more rotors and/or one or more] *a rotor or an* axial pump [elements for transforming rotational and/or axial force into the pumping force,] *element;* and

[at least one] *a* safe-lock [mechanism] *means* for preventing [mechanical action to cause] rotation of the [at least one or more rotors and/or] *rotor or* movement of the [one or more] axial pump [elements] *element,* thereby preventing [passage] *delivery* of the medicament[from the reservoir to the trans-dermal injection element unless a dose is requested]; *and*

*wherein* the separate [hand-held] drive device [being] *is* configured to be placed temporarily in proximity to the delivery device when a dose of medicament is required, the [hand-held] *separate* drive device comprising*:* an activation unit [for activating the control unit of the delivery device, the activation unit comprising at least one unlocking element to] *configured to* (*i*) provide energy to the control unit of the delivery device for unlocking the [at least one] safe-lock [mechanism] *means* and [a drive unit to] (*ii*) provide energy for [any of the one or more rotors and/or one or more] *the rotor or the* axial pump [elements] *element* of the control unit only when the separate [hand-held] drive device is in proximity to the delivery device[,]*;* and [wherein the hand-held drive device comprises] a sensor capable of detecting the amount of energy being transferred [and/or] *or* transformed into pumping force.

2. The system of claim 1, wherein the [at least one] *activation unit comprises an* unlocking element and [the] *a* drive unit, which cooperate [synergistically] to activate the control unit[in a specific manner as a key].

3. The system of claim 1, further comprising a magnetic key.

4. The system of claim 1, wherein the delivery device comprises a pump for pumping the medicament from the reservoir[to the trans-dermal injection element].

5. The system of claim 1, wherein*:* the delivery device comprises a base rotor[for holding]*; and* the reservoir *is disposed on the base rotor*.

6. The system of claim 1, wherein the [one or more rotors] *rotor* comprises [at least one] *a* primary rotor to transfer rotational force to a pump rotor.

7. The system of claim 6, wherein the [at least one] primary rotor and the pump rotor have the same axis of rotation.

8. The system of claim 6, wherein the [one or more rotors] *rotor* comprises [at least one] *a* secondary rotor to transfer rotational force to the [at least one] primary rotor.

9. The system of claim 8, wherein the [at least one] secondary rotor and the [at least one] primary rotor have the same axis of rotation.

10. The system of claim [6] *8*, wherein the control unit comprises a spring located between the pump rotor and the [at least one] primary rotor or between the [at least one] primary rotor and the [at least one] secondary rotor wherein the spring is loaded when [the] *a* drive unit is placed in proximity of the delivery device and is configured to transfer rotational force to the pump rotor while the drive device is being removed.

11. The system of claim 10, wherein the spring is a mainspring.

12. The system of claim 1, wherein [the one or more axial pump elements] *the axial pump element comprises a first axial pump element that* moves in an alternate direction along an axis with respect to movement of [the one or more] *a second* axial pump [elements] *element*.

13. The system of claim [12] *1*, wherein*:*

*the control unit comprises the axial pump element; and* the [one or more] axial pump [elements is] *element comprises* a membrane.

14. The system of claim 1, wherein*:*

*the control unit comprises the axial pump element and the rotor; and* the [one or more] axial pump [elements are] *element is* connected to the [one or more rotors] *rotor, wherein the rotor comprises a rotor* selected from the group consisting of: a base rotor, a pump rotor, a primary rotor, and a secondary rotor[, so that rotational force is transformed into axial force or vice versa].

15. The system of claim 1, wherein*:* the reservoir for holding the medicament [to be delivered] is a syringe-type reservoir comprising a first end and [at least one] *an* opening in [correspondence of] said first end for pumping medicament to [the] *a* trans-dermal injection element [and/or] *or* for introducing the medicament in the syringe-type reservoir, a second open end, and walls between [said] *the* first end and [said] *the* second end*;*

*the control unit comprises the axial pump element; and*

*the axial pump element comprises a first axial pump element configured to fit* into [which the one or more axial pump elements comprises a first axial pump element which fits] *the second open end of the syringe type reservoir* in a fluid-tight manner.

16. The system of claim 15, wherein the [control unit] *axial pump element* comprises a second axial pump element aligned with the syringe-type reservoir in [correspondence of said] *the* second open end, wherein the first axial pump element is adapted to move towards [said] *the* second axial pump element when the medicament is being introduced into the syringe-type reservoir.

17. The system of claim 16, wherein the second axial pump element transfers axial force to the first axial pump element [after] *in response to* the second axial pump element [has come into contact] *contacting* or [has engaged] *engaging* with the first axial pump element.

18. The system of claim 16, wherein the second axial pump element is attached to the first axial pump element [for pulling] *and is configured to pull* the first axial pump element towards the first end of the syringe-type reservoir when a dose of medicament is to be delivered.

19. The system of claim 1, wherein the control unit comprises a stabilization element for minimizing the moment of tilt of [any of the one or more rotors] the rotor [which are selected from the group consisting of: a base rotor, a pump rotor, a primary rotor, and a secondary rotor, or of the one or more axial pump elements] *or of the axial pump element*.

20. The system of claim 1, wherein the control unit comprises at least one directional element, allowing [any of the one or more rotors selected from the group consisting of: a base rotor, a pump rotor, a primary rotor, and a secondary rotor,] *the rotor* to rotate in a preferred direction [, and/or] *or* the [one or more] axial pump [elements] *element* to move in a preferred direction.

21. The system of claim 1, wherein [any of the one or more rotors] *the rotor* comprises [at least one] *a* magnet or a ferromagnetic [element] *material*.

22. The system of claim 1, wherein the [at least one] safe-lock [mechanism] *means* comprises a ferromagnetic [element or at least one] *material or a* magnet or a combination of different magnets configured so that only a specific corresponding magnetic field can be used to unlock the [at least one] safe-lock [mechanism] *means*.

23. The system of claim [1] *2*, wherein the [at least one] safe-lock [mechanism] *means* comprises a coil and the [at least one] unlocking element provides a specific magnetic field inducing a specific current in the coil when the drive device is placed in proximity of the delivery device[which provides electrical power for unlocking the at least one safe-lock mechanism for a specific period of time].

[24. The system of claim 1, wherein the at least one unlocking element comprises at least one magnet.]

25. The system of claim [1] *2*, wherein the drive unit provides rotational force [and/or] *or* axial force to the [one or more rotors and/or one or more] *rotor or the* axial pump [elements] *element* when the [hand-held] drive device is placed in proximity to the delivery device.

26. The system of claim [1] *2*, wherein the drive unit comprises electromagnets or a drive rotor or a drive element connected to a motor, the drive rotor or the drive element comprising at least one magnet.

27. The system of claim 1, wherein the separate [hand-held] drive device [is shaped as to form] *defines* a [complementary] cavity into which at least a [part] *portion* of the delivery device comprising the control unit substantially fits.

28. The system of claim 1, wherein the sensor is a Hall sensor.

29. The system of claim 1, wherein the [hand-held] drive device comprises at least one element to inform the user that [the] *a* dose has been delivered and that the [hand-held] drive device can be removed, or that an atypical situation has been encountered, the at least one element being selected from the group consisting of: a warning light, audio, a vibration signal, an alarm, and any combination thereof.

30. The system of claim 1, wherein the delivery [unit] *device* comprises an RFID chip [for being] *that is configured to be* identified by the [hand-held] drive device.

31. The system of claim 30, wherein the RFID chip is adapted to send a feedback signal [by being contacted] *in response to being* directly or indirectly *contacted* by moving the [one or more] axial pump [elements] *element*.

32. The system of claim [1] *2*, wherein the delivery device comprises a capacitor or *an* accumulator for receiving [and/or] *or* accumulating energy from the drive unit when the drive unit is placed in proximity of the delivery device.

*33. The system of claim 1, wherein the drive device is a hand-held drive device.*

*34. The system of claim 1, wherein the safe-lock means comprises at least one of a rod, a finger, one or more teeth, a spring, a ferromagnetic element, a magnet, a coil, a pivotable arm, or a clamp.*

*35. The system of claim 19, wherein the stabilization element comprises at least one of a rotor, a carved compartment, a chamber, a cavity, a groove, or a pin.*

* * * * *